United States Patent [19]
Bartelt et al.

[11] Patent Number: 5,488,956
[45] Date of Patent: Feb. 6, 1996

[54] ULTRASONIC TRANSDUCER ARRAY WITH A REDUCED NUMBER OF TRANSDUCER ELEMENTS

[75] Inventors: Hartmut Bartelt; Ekkert Bartosch; Peter Kraemmer, all of Erlangen, Germany

[73] Assignee: Siemens Aktiengesellschaft, Munich, Germany

[21] Appl. No.: 311,376

[22] Filed: Sep. 23, 1994

[51] Int. Cl.$^6$ .............................. A61B 8/00; H01L 41/04
[52] U.S. Cl. ...................... 128/662.03; 310/336
[58] Field of Search .................. 128/661.01, 662.03; 310/334, 357, 336, 358; 367/153

[56] References Cited

U.S. PATENT DOCUMENTS

| | | | |
|---|---|---|---|
| 2,837,728 | 6/1958 | Schuck | 340/9 |
| 2,928,068 | 3/1960 | Samsel | 340/10 |
| 4,518,889 | 5/1985 | T'Hoen | 310/357 |
| 4,658,176 | 4/1987 | Nakaya et al. | 310/334 |

FOREIGN PATENT DOCUMENTS

| | | |
|---|---|---|
| 3334090C2 | 3/1984 | Germany. |
| 3437862C2 | 5/1985 | Germany. |
| 3733776A1 | 4/1988 | Germany. |

OTHER PUBLICATIONS

Turnbull et al., "Beam Steering with Pulsed Two-Dimensional Transducer Arrays," *IEEE Transactions on Ultrasonics, Ferroelectrics, and Frequency Control*, vol. 38, No. 4, pp. 320–333 (Jul. 1991).

Martin et al., "A Simple Way to Eliminate Diffraction Lobes Emitted by Ultrasonic Transducers," *The Journal of the Acoustical Society of America*, vol. 49, No. 5 (Part 2), pp. 668–669 (May 1971).

Harris, "On the Use of Windows for Harmonic Analysis with the Discrete Fourier Transform," *Proceedings of the IEEE*, vol. 66, No. 1, pp. 51–83 (Jan. 1978).

*Primary Examiner*—Francis Jaworski
*Attorney, Agent, or Firm*—Kenyon & Kenyon

[57] ABSTRACT

An ultrasonic transducer array in which distances between the array's transducer elements ($T_{ij}$) increase in the direction of the rows (x direction) and in the direction of the columns (y direction) from a center of symmetry (S) outward. The integral over a straight-line function f(x) and/or g(y), which steeply decreases on either side of a center of symmetry (S) between the center points ($M_{ij}$) of adjacent transducer elements ($T_{ij}$), is constant for each row and/or column. Thus, the number of transducer elements ($T_{ij}$) is reduced without considerable deterioration of the beam characteristic of the transducer array.

18 Claims, 1 Drawing Sheet

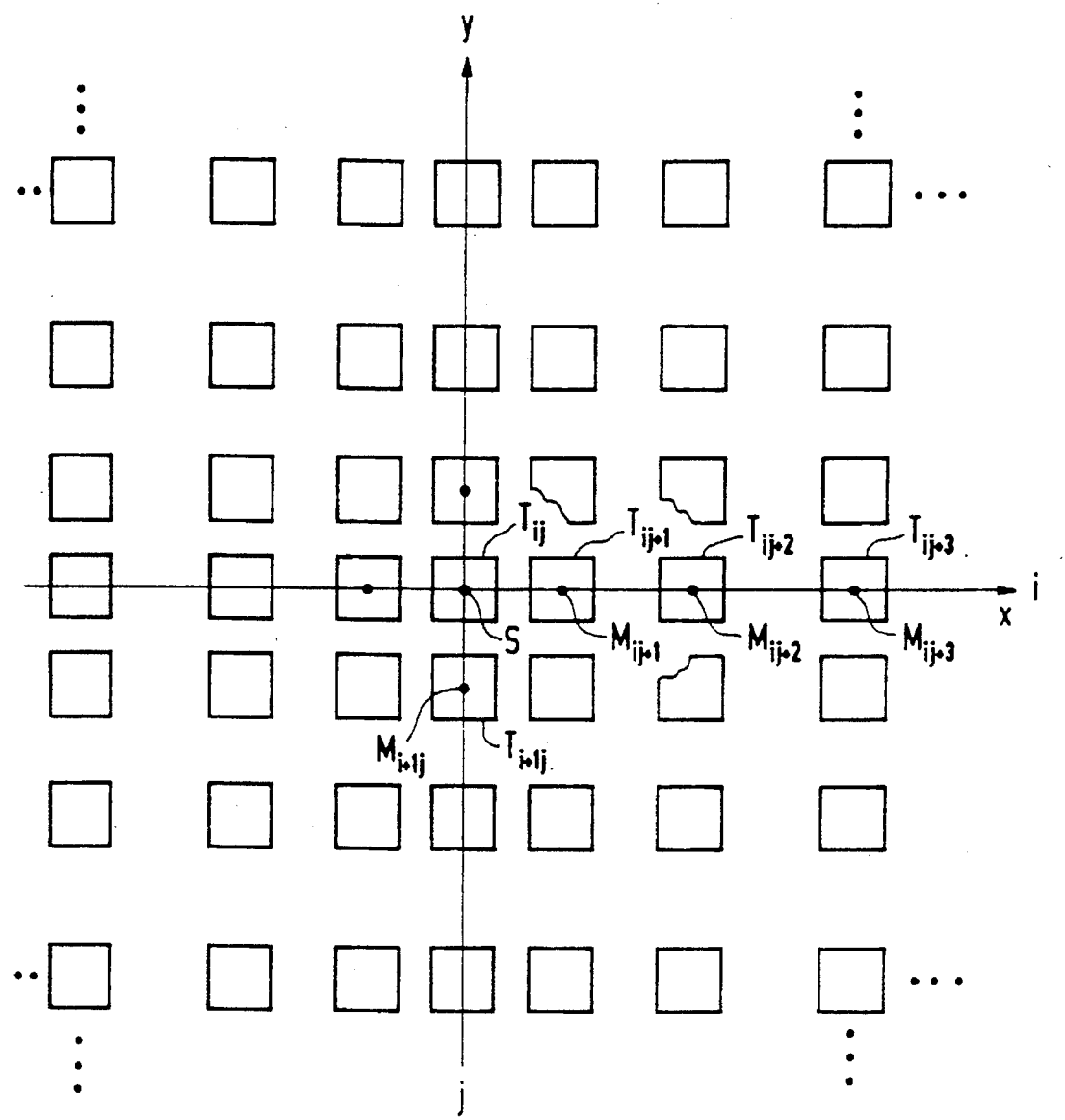

ULTRASONIC TRANSDUCER ARRAY WITH A REDUCED NUMBER OF TRANSDUCER ELEMENTS

BACKGROUND OF THE INVENTION

The present invention concerns an ultrasonic transducer array.

In medical ultrasound diagnosis, an area of the human body is exposed to ultrasound pulses. A signal processing unit constructs an ultrasound image, corresponding to a two-dimensional (2-D) section of the body, from the reflected ultrasound pulses. Typically, one-dimensional (1-D), and in particular linear, arrays of piezoelectric transducer elements, controlled by an electronic control unit with predefined phase delays, have been used to send and receive ultrasound pulses. With such linear arrays of piezoelectric transducer elements controlled with a phase delay, ultrasound beams can be transmitted, received, and focused at variable angles in the plane formed by the normal to the array surface and the longitudinal direction of the array. Generally, the angle, measured in relation to the normal for the ultrasound beam, increases as the transducer elements decrease in size.

Generally, the distance between the transducer elements is selected to be the same over the entire array and to be approximately equal to one-half of the ultrasound's wavelength. For example, when an examination frequency of 3.5 MHz is used, the spacing is equal to about 0.2 mm. This spacing is used to avoid additional diffraction patterns (side lobes). On the other hand, a minimum length of the linear array is required to achieve sufficient sound amplitude and accurate focusing of the beam. From these two requirements, i.e., from the maximum distance between the transducer elements and the minimum length of the array, a minimum number of transducer elements (typically 64) is derived for the array.

In addition to 1-D transducer arrays, two-dimensional (2-D) transducer arrays, and in particular matrix-shaped ultrasonic transducer arrays, are also known. These 2-D transducer arrays are typically formed by individual, rectangular, transducer elements. Matrix-shaped transducer arrays are known, for example, from German Patent No. C 34 37 862 and the corresponding U.S. Pat. No. 4,683,396 or from German Printed Application No. 37 33 776 and the corresponding U.S. Pat. No. 4,801,835.

If the transducer elements of the matrix arrays are controlled with predefined phase delays, an ultrasound beam, which is steerable and focusable in two angular directions, can be sent and detected. This is in contrast to linear arrays which are rotatable and focusable in only one angular direction. Thus higher image resolution is achieved with matrix arrays. To cover a sufficiently large spatial angle with the ultrasound beam, similar to the conditions for the linear array, when an examination frequency of 3.5 MHz is used, a maximum distance between the transducer elements is about 0.2 mm and a minimum surface area (aperture) of the 2-D array of typically about 20 mm×20 mm for a square array (i.e., an array in which the number of rows N=the number of columns M). Thus a minimum number of transducer elements is also required for the 2-D array, which may be 64×64=4096 for example.

For such a large number of transducer elements and the required small dimensions, the manufacturing and bonding of transducer elements and the number of control and data conductors required for the transfer of control and image signals represent a problem. Therefore, ways of reducing the number of transducers elements of the 2-D array, without appreciably deteriorating its beam sending and detecting characteristics are desired. In particular, the side lobes of the ultrasound should be greatly suppressed.

An ultrasonic transducer matrix typical for cardiography, with a square aperture (10 mm×10 mm) and transducer elements arranged evenly spaced in a square, is discussed in Turnbull et al., "Beam Steering with Pulsed Two-Dimensional Transducer Arrays," *IEEE Transactions on Ultrasonics, Ferroelectrics and Frequency Control*, Vol. 38, No. 4, pp. 320 through 333 (July 1991) ("the Turnbull article"). Since the transducer elements are spaced at less than one-half of the wavelength in the device discussed in the Turnbull article, side lobes are almost completely suppressed in the beam characteristic of this transducer matrix. Two methods based on the devices discussed in the Turnbull article are known for reducing the number of transducer elements. In the first method, transducer elements are removed from the corners of the matrix, which results in a transducer array with a circular aperture having a diameter corresponding to the side length of the original square. The transducer elements remain evenly spaced, so that the side lobes are still suppressed. However, the main lobes become somewhat wider. In the second method, transducer elements are removed from the matrix array using statistical selection. Thus the mean spacing of the transducer elements increases, and the intensity of the side lobes increases as the number of transducer elements remaining in the array decreases. Furthermore, the performance of the resulting transducer array is diminished.

U.S. Pat. No. 2,928,068 discusses a pressure wave transducer with a massive ceramic body. Electrodes are arranged on opposing surfaces of the ceramic body so that areas that are piezoelectrically activated in varying degrees are obtained. The degree of polarization of these areas decreases from the center of the ceramic body outward.

Martin et al., "A Simple Way to Eliminate Diffraction Lobes Emitted by Ultrasonic Transducers," *Journal of the Acoustical Society of America*, Vol. 49, No. 5 (Part 2), pp. 1668 through 1669 (May 1971) discusses an ultrasonic transducer with a massive quartz body. In the quartz body a Gaussian distribution is obtained for the amplitude of the ultrasound beam emitted, with a maximum in the center of the quartz body, via a special electrode arrangement.

German Patent No. C-33 34 090 (and the corresponding U.S. Pat. No. 4,518,889) discusses an ultrasonic transducer array with rod-shaped transducer elements arranged in parallel. The spacing between the transducer elements increases on either side of a central point so that the acoustic reaction of the effective surface of the array, and thus the polarization in response to even electrical excitation, decreases with the increasing distance from the central point or the central line according to a Gaussian function.

U.S. Pat. No. 2,837,728 discusses an ultrasonic transducer array with a plurality of identical transducer elements which are electrically evenly excited. The spacing of the transducer elements of the array increases from a centerline (symmetry axis) for a matrix-shaped array and from a center point outward for a circular array according to the mathematical formula $$\text{Distance} = k * \text{secant}(n*\theta),$$

where K is a constant, $\theta$ is a constant angle of about 10° and n is the number of transducer elements counted This relationship can be expressed as follows:

$$\int_{X_{ij}}^{X_{ij+1}} f(x)dx \approx \text{constant},$$

where $X_{ij}$ is the x coordinate of the center point $M_{ij}$ of the transducer element $T_{ij}$ and $X_{ij+1}$ is the x coordinate of the center point $M_{ij+1}$ of the transducer element $T_{ij+1}$. The definite integral $$\int_{X_{ij}}^{X_{ij+1}} f(x)dx,$$

corresponds to the surface area bounded by the abscissa (x axis), by the function f(x), and by two straight lines defined by $x=X_{ij}$ and $x=X_{ij+1}$. The ultrasonic transducer array can be a linear array with a single row or a two-dimensional, specifically matrix-shaped, array with a plurality of rows.

The present invention is based on the principle that the sensitivity of the transducer array at the array edge(s) can be reduced by varying the center point distances between the transducer elements according to the above criteria, without considerably deteriorating from the centerline or the center point.

The object of the present invention is to provide an ultrasonic transducer array where the number of transducer elements is reduced compared to an array with the same surface area and with an equidistant arrangement of the transducer elements and where, at the same time, the beam characteristic is not appreciably deteriorated.

SUMMARY OF THE INVENTION

The present invention attains this object by providing an ultrasonic transducer row or an array of transducer elements with at least one row (i) running in an X direction and columns (j), perpendicular to the at least one row, running in a Y direction. The distances between center points of adjacent transducer elements increases uniformly in each of the at least one row according to the following criteria:

(a) a linear function f(x), monotonously decreasing in the x direction on either side of a center of symmetry (S) with coordinates x=0 and y=0, is provided; and (b) the x coordinates of center points $M_{ij}$ of the transducer elements $T_{ij}$ in each row are selected so that the definite integral of function f(x) over x between the center points $M_{ij}$ and $M_{ij+1}$ of adjacent elements $T_{ij}$ and $T_{ij+1}$ is at least approximately constant. the beam characteristic, i.e., without substantially enhancing the side lobes and without substantially widening the main lobe.

In the embodiment of the present invention including a two-dimensional transducer array, the distance between adjacent transducer elements also preferably increases in each column (y direction) monotonously outward in the same way as in the rows, with a corresponding function g(y) for the columns. This relationship can be represented as follows:

$$\int_{Y_{ij}}^{Y_{i+1j}} g(y)dy \approx \text{constant},$$

where $Y_{ij}$ is the y coordinate of the center point $M_{ij}$ of the transducer element $T_{ij}$ and $Y_{i+1j}$ is the y coordinate of the center point $M_{i+1j}$ of the transducer element $T_{i+1j}$.

A function, such as a triangular function, Hanning, Hamming, Riesz, De la Vall-Puissin, Tukey, Bohman, Poisson, Hanning-Poisson, Cauchy, Gauss, Doph-Chebyshev, Kaiser-Bessel, Barilon-Femes, Exact Blackman, Blackman, minimum 3-sample Blackman-Harris or minimum 4-sample Blackman-Harris function is preferably selected for f(x) and/or g(y). These functions are known within the framework of a theoretical work for harmonic spectral analysis via discrete Fourier transform in signal recognition applications (see e.g., Harris, "On the Use of Windows for Harmonic Analysis with the Discrete Fourier Transform," *Proceedings of the IEEE*, Vol. 66, No. 1, pp. 51 through 83 (January 1978)). The Fourier transforms of these functions exhibit pronounced main lobes and relatively small side lobes. This property is used for the beam characteristic in this advantageous development according to the present invention.

BRIEF DESCRIPTION OF THE DRAWING

The FIGURE illustrates an embodiment of a matrix-shaped ultrasonic transducer array in accordance with the present invention.

DETAILED DESCRIPTION

A section of the central area of a transducer matrix in accordance with the present invention, around a center of symmetry S, is schematically shown in the FIGURE. The transducer elements T are preferably square-shaped. Transducer elements T form rows i and columns j of an M×N matrix (where $1 \leq i \leq M$ and $1 \leq j \leq N$) located in an orthogonal (x,y) system of coordinates with origin S=(0,0) and an x and y axis. Rows i run in the x direction and columns j run in the y direction. The ultrasonic transducer matrix can be square, i.e., the number of rows M is equal to the number of columns N. The matrix can also be rectangular, i.e., the number of rows M does not equal the number of columns N. The distances between the centers of elements in adjacent columns, for example, $M_{ij}$ and $M_{ij+1}$, $M_{ij+1}$ and $M_{ij+2}$, as well as $M_{ij+2}$ and $M_{ij+}$ increase from the center column j (at S=(0,0)) outward. Furthermore, a function f(x), representing spacing between rows i, and a function g(y), representing spacing between columns j, are symmetric with respect to the center of symmetry S, i.e., $f(x)=f(-x)$ and $g(y)=g(-y)$. For increasing values of the absolute values $|x|$ and $|y|$ the functions f(x) and g(y) decrease strictly monotonously. Thus, these functions f(x) and g(x) define window functions, which, in this embodiment disappear (i.e., are zero) at a selectable maximum value $\pm x_{max}$ and $\pm y_{max}$, i.e., $f(x_{max})= f(-x_{max})=0$ and $g(y_{max})=g(-y_{max})=0$. The boundaries of the window functions $\pm x_{max}$ and $\pm y_{max}$ can be located at either positive or negative function values.

Preferably both functions f and g are the same, i.e., $f(z)=g(z)$ for a real argument z.

In the embodiment illustrated, the center of symmetry S coincides with the center point $M_{ij}$ of a central transducer element $T_{ij}$. However, in an alternative embodiment, the center of symmetry S can be located outside of the individual transducer element surfaces.

From the given formula for the distances between center points $M_{ij}$ of transducer elements $T_{ij}$ it follows that at least the number N of columns j is greater than 3, and preferably also the number M of rows i.

The variation of the distances between the center points $M_{ij}$ of transducer elements $T_{ij}$ is only shown schematically and can also be corrected experimentally later to some degree.

What is claimed is:

1. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Hanning function that decreases monotonously on either side of the center of symmetry.

2. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Hamming function that decreases monotonously on either side of the center of symmetry.

3. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Riesz function that decreases monotonously on either side of the center of symmetry.

4. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a De la Vallé-Puissin function that decreases monotonously on either side of the center of symmetry.

5. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Tukey function that decreases monotonously on either side of the center of symmetry.

6. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Bohman function that decreases monotonously on either side of the center of symmetry.

7. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Poisson function that decreases monotonously on either side of the center of symmetry.

8. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Hanning-Poisson function that decreases monotonously on either side of the center of symmetry.

9. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Cauchy function that decreases monotonously on either side of the center of symmetry.

10. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points adjacent transducer elements is at least approximately constant and wherein said window function f(x) is a Gauss function that decreases monotonously on either side of the center of symmetry.

11. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Dolph-Chebyshev function that decreases monotonously on either side of the center of symmetry.

12. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Kaiser-Bessel function that decreases monotonously on either side of the center of symmetry.

13. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Barcilon-Temes function that decreases monotonously on either side of the center of symmetry.

14. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is an Exact Blackman function that decreases monotonously on either side of the center of symmetry.

15. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a Blackman function that decreases monotonously on either side of the center of symmetry.

16. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a minimum 3-sample Blackman-Harris function that decreases monotonously on either side of the center of symmetry.

17. An ultrasonic transducer array with at least one row running in an x direction of transducer elements, wherein in each row the distances between center points of adjacent transducer elements increase monotonously outward on either side of a center of symmetry with an x-coordinate x=0, wherein the x coordinates of the center points of the transducer elements in each row are selected so that a definite integral of a window function f(x) over x between center points of adjacent transducer elements is at least approximately constant and wherein said window function f(x) is a minimum 4-sample Blackman-Harris function that decreases monotonously on either side of the center of symmetry.

18. The ultrasonic transducer array according to one of claims 1 to 17 with at least three rows and at least three columns running in a y direction, perpendicular to the x direction, of transducer elements, wherein distances between center points of adjacent transducer elements also increase monotonously outward in each column.

* * * * *